United States Patent [19]

Martin et al.

[11] Patent Number: 4,657,932

[45] Date of Patent: Apr. 14, 1987

[54] METHOD OF TREATING PROLACTIN-RELATED DISORDERS

[75] Inventors: Joseph B. Martin, Belmont; William Millard, Quincy; Stephen Sagar, Boston, all of Mass.

[73] Assignee: Massachusetts General Hospital, Boston, Mass.

[21] Appl. No.: 643,761

[22] Filed: Aug. 24, 1984

Related U.S. Application Data

[63] Continuation of Ser. No. 375,540, May 6, 1982, abandoned.

[51] Int. Cl.$^4$ ............................................. A61K 31/13
[52] U.S. Cl. ..................................... 514/665; 514/899
[58] Field of Search ......................................... 514/665

[56] References Cited

FOREIGN PATENT DOCUMENTS 1141749  1/1969  United Kingdom ............... 424/325

OTHER PUBLICATIONS

Szabo et al. *Endocrinology*, vol. 109, #6, p. 225 (1981).
Horner et al. *Life Sciences*, vol. 29, p. 2437 (1981).
Prescott, et al. *Lancet*, 2:109–113 (1976).
Yudkoff et al. *New England J. of Medicine*, 304:141–145 (1981).
Williams, *Textbook of Endocrinology*, 5th ed. pp. 46–49, 75–77 (1974).
Thorne et al. *J. of Clinical Investigation*, vol. 58, pp. 180–189, Jul. 1976.
Lorenson et al. *Endocrinology*, vol. 110, No. 4, pp. 1164–1172 (Apr. 1981).
Simpkins, J. W. et al., *Endocrinology*, 112 No. 5, pp. 1889–1891 (1983),entitled "Cysteamine Depletes Prolactin in Young and Old Hyperprolactinemic Rats".
Millard, J. W. et al., *Endocrinology*, 113, No. 6, pp. 2161–2167, (1983), entitled "Cysteamine Induced Depletion of Both Immunological and Biological Prolactin Activity in the Anterior Pituitary and Blood of the Rat".
*Harrision's Principles of Internal Medicine*, 10th Edition, 1983, Index, p. 58, p. 600, subtitled "Hyperprolactinemia", p. 440, and p. 722.
Millard, W. J. et al., *Science*, vol. 217, pp. 452–454, (Jul. 1982), entitled "Cysteamine: A Potent and Specific Depletor of Pituitary Prolactin".
Millard, W. J. et al., Abstract 326, Annual Meeting of Endocrine Society held San Antonio Jan. 1983, entitled "Cysteamine-induced Depletion of Both Immunological and Biological Prolactin Activity in the Anterior Pituitary and Blood of the Rat".
Parsons, J. A. et al., Abstract 1182, Annual Meeting of Endocrine Society held San Antonio Jan. 1983, entitled "Effect of Cysteamine on Pituitary and Serum Prolactin Measured by Nb 2 Node Rat Lymphoma Cell Bioassay".
*Neuroendocrinology*, vol. 38, pp. 182–188, (1984), Saunders et al, "Cysteamine Acts Immediately to Inhibit Prolactin Release and Induce Cellular Changes in Estradiol–Primed Male Rats".
Parsons et al., *Endocrinology* 114:1812–1817 (1984), "Effects of Cysteamine on Pituitary, MtTW$_{15}$ Tumor, and Serum Prolactin Levels Measured by Rat Lymphoma Cell Bioassay and Radioimmunoassay".
Flückiger et al., *Effects of ergot Alkaloids on the Hypothalmic–Pituitary Axis*, Postgraduate Medical Journal, 1976, 52 (Suppl. 1), 57–61.
Harrison's *Principles of Internal Medicine*, Tenth Ed. (1983) pp. 600, 601, 722.
*The Merck Index*, 1976, pp. App–1.

*Primary Examiner*—Stanley J. Friedman
*Assistant Examiner*—Freda Abramson
*Attorney, Agent, or Firm*—Saidman, Sterne, Kessler & Goldstein

[57] ABSTRACT

A method of decreasing the concentration of prolactin in an animal, which comprises administering to the animal a prolactin-decreasing amount of cysteamine.

5 Claims, No Drawings

METHOD OF TREATING PROLACTIN-RELATED DISORDERS

BACKGROUND OF THE INVENTION

The present invention arose out of work sponsored by the National Institutes of Health under Grant AM26252.

This application is a continuation of application Ser. No. 375,540, filed May 6, 1982, now abandoned.

1. Field of the Invention

The present invention relates to the treatment of prolactin-related disorders, especially conditions where the levels of prolactin are to be decreased.

2. Description of the Prior Art

Prolactin is an anterior pituitary hormone secreted by the lactotrophs. Both the number of lactotrophs and the pituitary content of prolactin increase during pregnancy. Human prolactin has a molecular weight of approximately 20,000. A large form of prolactin, possibly a prohormone (molecular weight approximately 40,000), comprises a small fraction of the circulating prolactin in normal subjects, but may be increased in blood of patients with pituitary tumors. Similarities and homologies exist among human prolactin, growth hormone and the placental hormone placental lactogen, but these can nevertheless be distinguished since specific radioimmunoassays for prolactin are now available.

The only clearly established physiological function for prolactin in humans relates to lactation in females. The exact mechanism of prolactin action on the breast is not known. Whether the hormone has any function in males is also unknown. Receptors for prolactin are present in the kidney, liver, adrenal gland, heart and gonads. Over 85 actions of prolactin have been described in other animals, many of these actions relate to the gonad, or to synergism with steroid hormones from the gonads or adrenal glands. Prolactin has a clear osmoregulatory function in some fish through an action on the gills, and also appears to affect organ growth in some animals.

The normal range for plasma prolactin is 1 to 25 ng/ml for women and 1 to 20 ng/ml for men. The higher mean levels in women are probably the result of a stimulatory effect of estrogens on prolactin secretion. Secretion of prolactin in normal subjects is episodic and the half time in the blood is approximately 20 minutes, resulting in oscillations of blood levels during the day. Prolactin concentration in plasma gradually increases in pregnancy. Nipple or breast stimulation, particularly during nursing, causes a rapid rise in serum prolactin levels. Other factors that cause prolactin release are stress (including hypoglycemia), strenuous exercise, surgery and sexual intercourse (in women). All of these stimuli suggest a neurally derived mechanism for the control of prolactin secretion.

The regulation of prolactin secretion is controlled by neurally derived factors from the brain, primarily located within the hypothalamus, and also by sex steroids. There is evidence that prolactin can also regulate its own secretion via a short-loop negative feedback mechanism. Prolactin is unique amongst anterior pituitary hormones in that it is under a tonic hypothalamic inhibitory influence. Evidence for this stems from studies in which pituitary stalk sectioning, anterior pituitary transplantation and destruction of the hypothalamus all result in increased prolactin secretion.

Dopamine appears to be the major substance from the hypothalamus which inhibits prolactin secretion. Dopamine or its receptor agonists administered in vivo or in vitro inhibit, while dopamine receptor antagonists stimulate, prolactin secretion. The principal dopamine neural pathway involved in prolactin regulation is the tuberoinfundibular dopamine pathway (TIDP). TIDP-cell bodies in the arcuate/periventricular area of the hypothalamus send their axons to terminate on hypophysial portal blood vessels in the median eminence. Two major lines of evidence indicate that dopamine may be the "native" prolactin inhibiting factor (PIF). First, exogenously administered dopamine in concentrations similar to those found in portal blood effectively lowers prolactin secretion both in vivo and in vitro. Second, specific dopamine receptors are present in the anterior pituitary on lactotroph cell membranes.

There is also evidence that a prolactin releasing factor (PRF) exists; however, its identity is not known. Two peptides, thyrotropin releasing hormone (TRH) and vasoactive intestinal polypeptide (VIP), are possible candidates for PRF because they have been found to act directly on the anterior pituitary to increase prolactin secretion. Other peptides such as substance P, beta-endorphin, and met-enkephalin have also been shown to elevate prolactin but their actions appear to be indirect.

Brain monoamines other than dopamine are also involved in the control of prolactin secretion. Norepinephrine and serotonin both appear to elevate prolactin. The suckling response as well as the morphine-induced and stress-induced increases in prolactin, appear to be mediated by serotonergic mechanisms. The physiological role of norepinephrine in prolactin regulation has not been clearly defined but there is evidence that norepinephrine may be involved in the estrogen-induced prolactin rise.

Disorders in Prolactin Secretion

Hypoprolactinemia is infrequently found in humans. When observed it is often associated with pituitary necrosis and infarction such as that which is found in Sheehan's syndrome. Except for the fact that patients fail to lactate, no other endocrine disorder has been attributed to reduced prolactin secretion.

On the other hand, hyperprolactinemia is an often encountered pituitary dysfunction. The most frequently observed clinical feature of hyperprolactinemia in both men and women is impaired gonadal function. In hyperprolactinemic women, a spectrum of menstrual irregularities are found including amenorrhea (often associated with galactorrhea), oligomenorrhea, polymenorrhea and regular menses with associated infertility. Hyperprolactinemic men may present with impotence and loss of libido; rarely gynecomastia and galactorrhea occur.

In approximately 20-30% of patients with elevated prolactin levels, a pituitary adenoma is found to be the underlying cause. Hyperprolactinemia can also be demonstrated in conditions in which no pituitary tumor is found. These usually reflect a disturbance of the central control mechanisms for prolactin regulation either as a result of hypothalamic disease or due to alterations in normal dopamine regulation. Patients using psychotropic, antihypertensive and antiemetic drugs often show elevated prolactin levels. All of these drugs are either dopamine receptor antagonists or interfere with the synthesis or release of dopamine.

Patients with hyperprolactinemia have three possible courses of treatment: surgery, radiotherapy and medical therapy. Radiotherapy often does not reestablish normal prolactin levels, fertility or gonadal function. Currently, medical therapy with dopamine agonists is the treatment of choice for most patients with hyperprolactinemia.

Bromocriptine (2-alpha bromergocriptine), an ergot alkaloid drug with potent dopamine-like activity, has received the most attention for use in hyperprolactinemia therapy. Bromocriptine (Parlodel ®)) treatment effectively lowers prolactin and restores normal gonadal function in nearly 80% of patients. In humans there is evidence that bromocriptine can lead to a reduction in tumor size. One proposed mechanism by which bromocriptine reduces tumor growth may be through a direct action on mitotic activity since bromocriptine inhibits DNA synthesis in pituitary cells.

There are some adverse side-effects of bromocriptine therapy which are generally mild to moderate in degree. These include postural hypotension, headache, dizziness, and nausea and vomiting. During pregnancy the use of bromocriptine is generally discontinued. There have been reports that bromocriptine may be teratogenic in rabbits but this claim has not been substantiated in humans or other animal species. The occurrence of congenital malformations in offspring of patients receiving bromocriptine was no greater than that observed in normal, spontaneous pregnancies.

Cysteamine: Its Effects on Biological Processes

Cysteamine (2-mercaptoethylamine) is a thiol reagent whose biological activities have been extensively investigated. Experimentally, it has been used as a radioprotective agent (see Bacq "Chemical Protection Against Ionizing Radiation", Charles C. Thomas, Springfield Ill. (1965)), and as an ulcerogen in rats (Selye, H. and Szabo, S., Nature 244: 458-459 (1973)). Clinically, it has been used in the treatment of acetaminophen (Tylenol) poisoning (Prescott, L. F. et al, Lancet 2: 109-113 (1976)) and, more recently, in the treatment of cystinosis (Yudkoff, M. et al New England Journal of Medicine 304: 141-145 (1981)). Szabo and Reichlin (Regulatory Peptides 1, Suppl. 1: Slll (1981)), in the course of studying the ulcerogenic properties of cysteamine, found that the oral administration of cysteamine produces an acute, partial depletion of somatostatin-like immunoreactivity in the gastrointestinal tract and hypothalamus of rats. Also, Szabo et al (Endocrinology 109: 225 (1981)) disclosed the use of cysteamine to destroy somatostatin. They reported that cysteamine destroyed somatostatin throughout tissues of the body 4 to 7 hours after administration, and suggested that cysteamine acts at the cellular level to cause the breakdown of preformed hormone. Horner et al (Life Sciences 29: 2437 (1981)) disclose the effect of cysteamine on peripheral catecholamine levels. In spite of these biological effects of cysteamine, no one, prior to this invention, had yet investigated the effects of cysteamine on prolactin levels.

Because of the problems associated with excess prolactin levels in animals, a need continues to exist for a rapid, efficient and selective therapeutic method to decrease such levels.

SUMMARY OF THE INVENTION

It is therefore an object of the invention to provide a method for decreasing prolactin levels in animals.

It is another object of the invention to provide a method for the treatment of hyperprolactinemia related disorders, such as galactorrhea, amenorrhea, and infertility.

These and other objects of the invention as will hereinafter become more readily apparent have been attained by providing:

a method of decreasing the concentration of prolactin in an animal, which comprises:

administering to said animal a prolactin decreasing amount of cysteamine.

DESCRIPTION OF THE PREFERRED EMBODIMENTS

The present invention derives from the discovery that administration of cysteamine to animals causes a dramatic and rapid decrease on the levels of pituitary prolactin. Immunoreactive prolactin is reduced to less than 5% of control values in both serum and anterior pituitary of rats within 2 hours after administration of cysteamine 300 mg/kg subcutaneously, with no significant effect on pituitary content of growth hormone, TSH (thyroid stimulating hormone), FSH (follicle stimulating hormone) or $\beta$-lipotropin. Cysteamine at this same dose reduces pituitary LH (luteinizing hormone) content by approximately 50%. Lower doses of cysteamine (90 milligrams per kilogram) have no effect on pituitary LH concentrations but reduce pituitary prolactin to less than 10% of control levels. Even at the $ED_{50}$ concentration of 30 milligrams per kilogram, prolactin is still inactivated, and the inactivation is reversible in 24-72 hours.

Cysteamine destroys prolactin as measured by radioimmunoassay both in vitro in cell cultures and in vivo in the intact rat. However, cysteamine does not seem to affect purified prolactin in vitro. Pretreatment of cultured anterior pituitary cells with potent dopamine receptor antagonists (domperidone and spiperone) does not affect cysteamine's action on prolactin. This indicates that cysteamine does not act through the dopamine receptor to cause its prolactin-depleting effects; thus, its action represents a novel, heretofore not described effect. By electron microscopy, cysteamine was not found to alter the prolactin-secretory granule or to induce prolactin degradation by lysosomes, thus indicating that this drug does not alter lactotrope cellular morphology. Therefore, by a presently unknown mechanism which is different from that of bromocriptine, cysteamine causes the loss of immunoreactivity of PRL in the whole animal.

Prolactin is a large polypeptide hormone with three disulfide linkages. Its structure closely resembles that of growth hormone (GH) (Williams, "Textbook of Endocrinology" page 46). Growth hormone, however, is relatively resistant to inactivation by cysteamine, emphasizing the unexpected aspect of the observed results. (The levels of GH in animals can be affected by cysteamine, although not directly, but by the action of cysteamine on somatostatin, which in turn regulates GH levels.)

Cysteamine administration to an animal in vivo can be carried out in order to generally decrease levels of prolactin in said animal, including both circulating or pituitary levels, or, more preferably, to treat conditions wherein the prolactin levels are abnormally elevated, i.e. above the mean plasma level. These levels are about $6.2 \pm 0.6$ ng/ml for normal men, and $9.0 \pm 0.6$ ng/ml for women, (Endocrinology, Williams, 48). While the difference between the means is significant, there is a major overlap of the two groups.

Among the abnormal conditions which can also be treated with cysteamine according to the present invention, are those for which the ergot alkaloids, such as bromocryptine, have been used in the prior art. They include galactorrhea, infertility, impotence, resumption of normal menstural cycles in patients with amenorrhea, and ectopic prolactin production.

Any animal suffering from hyperprolactinemia can be treated with cysteamine according to the present invention. These include especially the mammals, and most especially humans of both sexes.

The administration dose will depend on the type of animal, the age and sex of the subject, other concurrent conditions, contraindications, mode of administration, and the like. Generally, a daily dosage of from 30 mg/kg to 300 mg/kg, 1 to 6 times per day will be sufficient.

Administration can be subcutaneous, oral, intraperitoneal, intravenous, intraarterial, and intramuscular. The preferred mode of administration is oral.

Cysteamine (which is commercially available) can be administered alone or in the presence, or admixed with, an appropriate pharmacologically inert carrier such as distilled water or saline.

Having now generally described this invention, the same will become better understood by reference to a specific example which is included herein for purposes of illustration only and is not intended to be limiting of the invention or any embodiment thereof.

EXAMPLE

Administration of cysteamine to rats reduced immunoreactive prolactin to less than 5% of control values in both serum and anterior pituitary within 2 hours after administration of 300 mg/kg, subcutaneous, with no significant effect on pituitary content of growth hormone, TSH or $\beta$-lipotropin. The effect of immunoreactive prolactin occured with an $ED_{50}$ of 30 mg/kg and was reversible, with plasma levels returning to normal within 24 hours and pituitary content within 72 hours. At 1 and 2 hours following a dose of 300 mg/kg, the pituitary appeared normal by electron microscopy; mammotrophs containing normal appearing secretory granules could be readily identified. In dispersed rat anterior pituitary cells in tissue culture, cysteamine added to the medium depleted immunoreactive prolactin in cells to less than 10% of control values. The depletion was maximal by 1 hour, had an $ED_{50}$ of 0.3 mM and was reversible. The depletion of immunoreactive prolactin in vitro was not blocked by $10^{-7}M$ domperidone, or $10^{-7}M$ spiper one, two dopamine receptor antagonists.

Cysteamine does not interfere with the radioimmunoassay for immunoreactive prolactin at concentrations 30-fold in excess of those present in these experiments. Therefore, cysteamine is a potent and relatively specific agent which depletes the rat pituitary of immunoreactive prolactin by a novel mechanism, not due to increased release of immunoreactive prolactin, not mediated by pituitary dopamine receptors, and not accompanied by morphologic evidence of damage to the mammotrophs.

Having now fully described this invention it will be apparent to one of ordinary skill in the art that the same can be performed within a wide and equivalent range of parameters, conditions, modes of administration, pharmacologic compositions, and the like, without affecting the spirit or scope of the invention, or of any embodiment thereof.

What is claimed as new and intended to be covered by Letters Patent of the United States is:

1. A method of decreasing the concentration of prolactin in a hyperprolactinemic animal, which comprises: administering to said animal a prolactin-decreasing amount of cysteamine.

2. The method of claim 1 wherein said animal is a human.

3. The method of claim 2 wherein said human is suffering from amenorrhea caused by hyperprolactinemia.

4. The method of claim 1 wherein said cysteamine is administered in an amount of from 30 to 300 mg/kg/day.

5. The method of claim 1 wherein said cysteamine is administered together with an inert pharmacological carrier.

* * * * *